(12) United States Patent
Samuel et al.

(10) Patent No.: US 9,877,949 B2
(45) Date of Patent: Jan. 30, 2018

(54) ANTICANCER TREATMENT METHODS INVOLVING ANALOGS AND DERIVATIVES OF 3-(2-SUBSTITUTED-ETHYL) INDOLE COMPOUNDS

(71) Applicant: TUSKEGEE UNIVERSITY, Tuskegee, AL (US)

(72) Inventors: Temesgen Samuel, Tuskegee, AL (US); Teshome Yehualaeshet, Tuskegee, AL (US); Tesfaye Serbessa, Elizabeth City, NC (US); Khalda Fadlalla, Tuskegee, AL (US)

(73) Assignee: TUSKEGEE UNIVERSITY, Tuskegee, AL (US)

( * ) Notice: Subject to any disclaimer, the term of this patent is extended or adjusted under 35 U.S.C. 154(b) by 23 days.

(21) Appl. No.: 14/568,730

(22) Filed: Dec. 12, 2014

(65) Prior Publication Data

US 2015/0164860 A1    Jun. 18, 2015

Related U.S. Application Data

(60) Provisional application No. 61/917,192, filed on Dec. 17, 2013.

(51) Int. Cl.
| | |
|---|---|
| *C12N 5/00* | (2006.01) |
| *A61K 31/404* | (2006.01) |
| *C07D 209/10* | (2006.01) |
| *A61K 45/06* | (2006.01) |

(52) U.S. Cl.
CPC .......... *A61K 31/404* (2013.01); *A61K 45/06* (2013.01); *C07D 209/10* (2013.01)

(58) Field of Classification Search
CPC .............. A61K 31/404; A61K 2300/00; A61K 45/061; C07D 209/10
See application file for complete search history.

(56) References Cited

PUBLICATIONS

Folks et al. Biochem. Pharmacol. (2001): 61: 129-136.*
Bertino et al. In "Cecil Textbook of Medicine" Goldman and Bennet, Eds. (2000) 21st Edition vol. 1, pp. 1060-1074 (W.B. Saunders Company: Philadelphia PA).*
Gura, T. Science (1997) 278: 1041-1042.*
Kaiser, J. Science (2006) 313: 1370.*

* cited by examiner

*Primary Examiner* — Susan Hanley
(74) *Attorney, Agent, or Firm* — Hogan Lovells US LLP

(57) ABSTRACT

Methods for inhibiting cancer cell proliferation and killing cancer cells are disclosed. Such methods comprise treating cancer cells with an indole compound having the structure of formula (I):

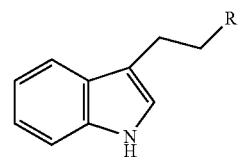

wherein R is defined herein.

9 Claims, 20 Drawing Sheets

I3C

BEI-9

ANTICANCER TREATMENT METHODS INVOLVING ANALOGS AND DERIVATIVES OF 3-(2-SUBSTITUTED-ETHYL) INDOLE COMPOUNDS

This invention was made with government support under grant number SC2CA13787, U54CA118948, and SC3GM109314 awarded by the National Institutes of Health. The government has certain rights in the invention.

BACKGROUND OF THE INVENTION

An aspect of this invention relates to novel methods of killing cancer cells and inhibiting cancer cell proliferation by treating cancer cells with 3-(2-substituted-ethyl) indole compounds. The National Cancer Institute estimates that as of Jan. 1, 2012, approximately 13.7 million Americans had some history of cancer; some being cancer-free survivors, while others still having evidence of cancer and undergoing treatment. About 1,660,290 new cancer cases are expected to be diagnosed in 2013. Worse yet, in 2013, about 580,350 Americans are expected to die of cancer, almost 1,600 people per day. Cancer is the second most common cause of death in the United States, exceeded only by heart disease. Cancer accounts for nearly 1 of every 4 deaths. The bleak picture becomes brighter: the 5-year relative survival rate for all cancers diagnosed between 2002 and 2008 is 68%, up from 49% from the period 1975-1977. The improvement in survival rates reflects both progress in diagnosing cancer at earlier stages and improving treatment options. The present invention expands the field of treatment options available to those fighting this nefarious disease.

Of all cancer types, colorectal cancer is one of the most frequently diagnosed. Excluding skin cancers, colorectal cancer is the third most common cancer diagnosed in both men and women in the United States. The American Cancer Society projects the following estimates for 2013: 102,480 new cases of colon cancer and 40,340 new cases of rectal cancer. Colorectal cancer is the third leading cause of cancer-related deaths in the United States when men and women are considered separately, and the second leading cause when both sexes are combined. It is expected to cause about 50,830 deaths during 2013.

The odds of surviving cancer increase significantly if the disease is detected in an early localized stage. Unfortunately, only about a third of cancer diagnoses occur at this early stage. To combat later-stage cancer, medical professionals prescribe the following types of treatment: surgery, radiation therapy, chemotherapy, targeted therapy, or any combination thereof. Chemotherapy drugs and targeted therapy drugs are both used to treat cancer. Derivative compounds of such drugs continue to be studied and tested. Indole compounds have been investigated for their putative anticancer properties. For example, indole-3-carbinol is a natural bioactive compound present in cruciferous vegetables such as cabbage, broccoli, and collard greens. Studies have indicated the efficacy of indole-3-carbinol and its acid-induced dimerization product, 3,3' diindolylmethane (DIM) against various human cancers. Additionally, indole compounds have been shown to have multiple intracellular targets through which they affect cancer cell signaling. These effects are significant with respect to chemosensitization. Indole-3-carbinol, DIM, and various other indole derivatives help reduce the toxicity of and resistance against conventional chemotherapeutic drugs. Both indole-3-carbinol and DIM are well known for their clinical benefits; however, research inversely correlating indole-3-carbinol with the viability of cancer cells is limited and inconsistent.

SUMMARY OF THE INVENTION

The present invention provides a method of inhibiting cancer cell proliferation and killing cancer cells, comprising treating cancer cells with an indole compound, or the pharmaceutically acceptable salt thereof, having the structure of the following formula (I):

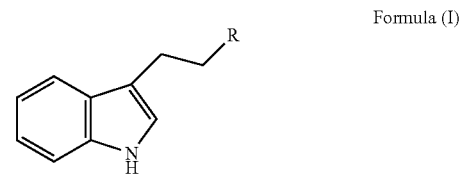

Formula (I)

wherein R is selected from the group consisting of: a halogen, alkyl, alkyl halide, acyl halide, aldehyde, ester, hydroxyalkyl, carboxyl, carboxyalkyl, benzyl, benzylakyl, sulfonate, alkyl sulfonate, and sulfonamide. Exemplary compounds of the invention include, but are not limited to the following compounds: 3-(2-bromoethyl) indole, 3-(2-hydroxyethyl) indole, indole-3-thiocarboxamide, indole-3-propionic acid, 3-(methoxymethyl)-1H-indole, ethyl indole-3-carboxylate, indole-3-acetic acid sodium, indole-3-acetamide, indole-3-acetic hydrazide, ethyl indole-3-carboxylate, and 3-(trifluoroacetyl)indole.

Derivatives and analogs of 3-(2-substituted-ethyl) indole compounds have the potential to be used as anticancer agents for research, chemoprevention, or as adjuvant therapeutics in combination with other agents.

Also disclosed is a method of killing cancer cells, comprising treating cancer cells with an indole compound having the structure of formula (I), wherein R is selected from the group consisting of: a halogen, aldehyde, alkyl, hydroxyalkyl, carboxyl, carboxyalkyl, benzyl, benzylakyl, sulfonate, alkyl sufonate, and sulfonamide; and a pharmaceutically acceptable salt thereof wherein the treated cancer cells are killed after treatment with the indole compound. An indole compound that is particularly useful in killing colon cancer cells includes the compound having the structure of formula (I), wherein R represents bromine. Other useful treatments include treating cancer cells with a compound selected from a group consisting of 3-(2-bromoethyl) indole, 3-(2-hydroxyethyl) indole, indole-3-thiocarboxamide, indole-3-propionic acid, 3-(methoxymethyl)-1H-indole, ethyl indole-3-carboxylate, indole-3-acetic acid sodium, indole-3-acetamide, indole-3-acetic hydrazide, ethyl indole-3-carboxylate, and 3-(trifluoroacetyl)indole.

Another embodiment of the present invention is a method of inducing apoptosis in cancer cells, comprising: treating the cancer cells with a combination of TNFα and an indole compound having the structure of formula (I), wherein R is selected from the group consisting of: a halogen, aldehyde, alkyl, hydroxyalkyl, carboxyl, carboxyalkyl, benzyl, benzylakyl, sulfonate, alkyl sufonate, and sulfonamide. One useful indole compound is the indole compound having the structure of formula (I), wherein R represents bromine. The indole compound is administered at a concentration of at least 0.5 µM, or at least 0.8 µM, or ranging from 1.0 µM to 10 µM.

Another method of inducing apoptosis in cancer cells comprises treating the cancer cells with a combination of one or more chemotherapeutic drugs and an indole compound having the structure of formula (I), wherein R is selected from the group consisting of: a halogen, aldehyde, alkyl, hydroxyalkyl, carboxyl, carboxyalkyl, benzyl, benzylakyl, sulfonate, alkyl sufonate, and sulfonamide. Such method is also effective where the one or more chemotherapeutic drugs is camptothecin or a camptothecin-analog. Useful comptothecin-analogs include topotecan and irinotecan. In such a combination treatment, cancer cells are treated firstly with the one or more chemotherapeutic drugs, and after a predetermined waiting period, treated secondly with the indole compound. An effective waiting period is at least 24 hours.

BRIEF DESCRIPTION OF THE DRAWINGS

FIG. 2 indicates that while the vehicle control cells multiplied and filled the growth surface, those cells treated with 3-(2-bromoethyl) indole did not show any sign of proliferation, thus suggesting the growth inhibitory activity of the 3-(2-bromoethyl) indole compound. This figure shows that 3-(2-bromoethyl) indole is a potent inhibitor of cell proliferation.

FIG. 4 shows marked reduction in cell viability was attained by treating the cells with 3-(2-bromoethyl) indole, even at a concentration of 12.5 µM. X-axis indicates the concentration used, and y-axis indicates the relative viability index compared to the vehicle treated cells.

FIG. 6 reveals that 3-(2-bromoethyl) indole decreases the viability index of the cancer cells, as measured by MTS assay. The absorbance reading at 490 nm wavelength, representing cell viability index as measured through MTS assay, is shown on Y-axis.

FIG. 8 shows microphotographs taken at the beginning of the experiment (t0), 48, and 96 hours after the treatment. FIG. 9 shows a graphical depiction of how the wound gap decreases over time, with measurements taken at (t0), 25, 48, 72, and 96 hours after the treatment. The wound gap is, of course, largest at t0, but the results show that the sample treated with BEI-9 prevents the gap from closing by any significant margin.

FIG. 11 shows that by applying immunoblotting techniques, 3-(2-bromoethyl) indole treatment decreased the expression of cyclin A protein and cyclin D protein.

FIG. 12 shows the relative reporter cell activity measured 24 hours after treatment with either the control vehicle (DMSO) or any one of the fourteen tested indole compounds. FIG. 12 reveals that 3-(2-bromoethyl) indole (#9 on the graph) reduced the reporter cell activity significantly as compared to the control and the other tested indole compounds.

FIG. 13 illustrates that treatment with 5 µM and 10 µM 3(2-bromoethyl) indole completely abolishes NF-kB reporter activity that was activated by TNFα.

FIG. 14 also reveals that a co-treatment of TNFα and 3-(2-bromoethyl) indole results in the appearance of cells with membrane blebs, which is an indication of cell apoptosis.

FIG. 15B shows that ATP-dependent cell viability was measured using a cell-TiterGlo kit. As the luminescence activity is roughly the same for cells treated with the control as those treated with BEI-9, FIG. 15B suggests that BEI-9 does not inhibit luciferase by competing with ATP.

FIG. 16 shows that 3-(2-bromoethyl) indole inhibited the NF-kB response by more than 50% at concentrations greater than 0.8 µM. As can be seen, the dual treatment of camptothecin and 3-(2-bromoethyl) indole at BEI-9 concentrations greater than 0.8 µM inhibits the NF-kB response by more than 50% of a camptothecin-only treatment.

DETAILED DESCRIPTION OF THE INVENTION

Figure 1A:
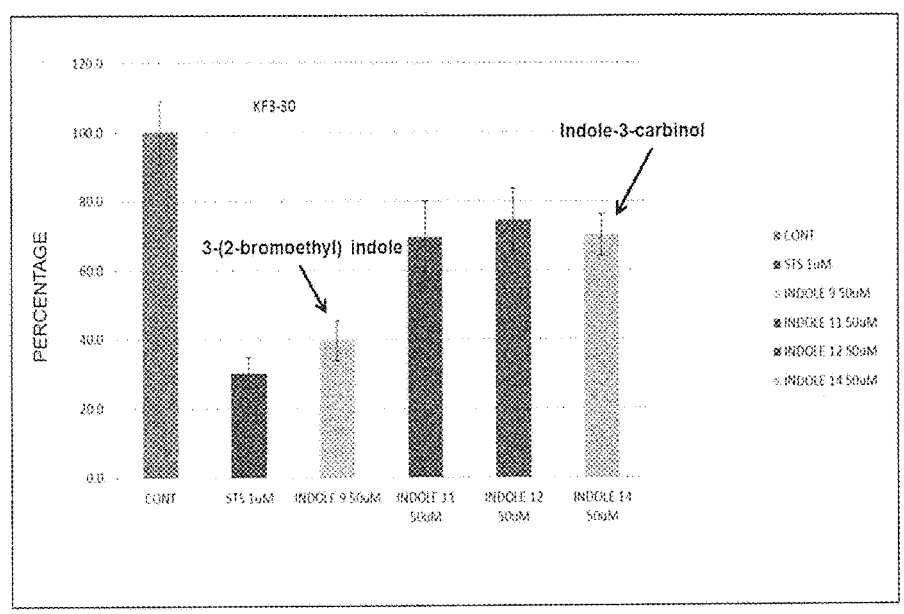
FIG. 1A compares the relative bioactivities of 3-(2-bromoethyl) indole and three other indole derivative compounds, each having been tested on cancer cells, as discussed in Example 1 herein. "Indole 9" listed in the figure represents 3-(2-bromoethyl) indole and "Indole 14" listed in the figure represents indole-3-carbinol. In certain instances, the compound 3-(2-bromoethyl) indole is referred to herein as "BEI-9."
Figure 1B:
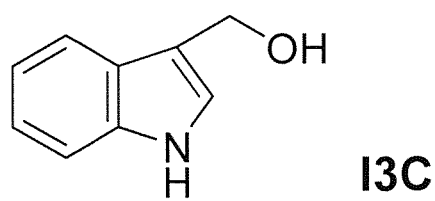
FIG. 1B depicts the chemical structures of indole-3-carbinol (I3C) and 3-(2-bromoethyl) indole.
Figure 1B:
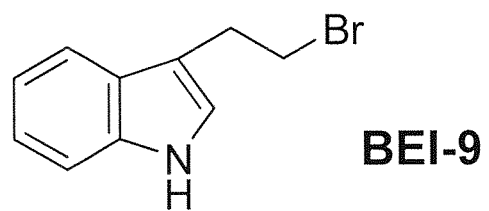

Indole-3-carbinol and its acid-induced dimerization product DIM have been shown to have multiple intracellular targets through which the compounds affect cancer cell signaling. Both compounds are well known as cancer preventative compounds or chemosensitizer molecules. Variations of the structure common to indole-3-carbinol and DIM—namely, the aromatic, heterocyclic indole compound—were analyzed for bioactivity on cancer cells. After functional screening, it was unexpectedly discovered that 3-(2-substituted-ethyl) indole compounds displayed higher bioactivity on cancer cells than indole-3-carbinol. It is to be understood that the following descriptions are exemplary and explanatory only. References to various embodiments are merely made to aid those skilled in the art in comprehending the teachings of the present invention.

One aspect of the present invention provides a method of inhibiting cancer cell proliferation by treating cancer cells with a 3-(2-substituted-ethyl) indole compound having the structure of formula (I):

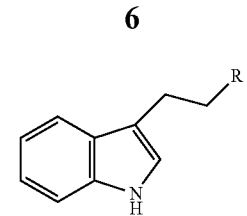

wherein R is selected from the group consisting of: a halogen, aldehyde, alkyl, hydroxyalkyl, carboxyl, carboxyalkyl, benzyl, benzylakyl, sulfonate, alkyl sulfonate, and sulfonamide. Moreover, the 3-(2-substituted-ethyl) indole compounds may be in the form of pharmaceutically acceptable salts. Such modifications are known in the art and include those that increase biological penetration into a given biological system, increase oral bioavailability, increase solubility to allow treatment by means of injection, and the like. Exemplary compounds of the invention include, but are not limited to: 3-(2-bromoethyl) indole, 3-(2-hydroxyethyl) indole, indole-3-thiocarboxamide, indole-3-propionic acid, 3-(methoxymethyl)-1H-indole, ethyl indole-3-carboxylate, indole-3-acetic acid sodium, indole-3-acetamide, indole-3-acetic hydrazide, ethyl indole-3-carboxylate, and 3-(trifluoroacetyl) indole.

Alternative embodiments of the present invention provide for methods of inhibiting cancer cell proliferation comprising treating cancer cells with a 3-(2-substituted-ethyl) indole compound having the structure of the aforementioned formula (I), wherein the R represents a substituent selected from the following group: bromine, fluorine, chlorine, methyl, ethyl, hydroxymethyl, and hydroxyethyl.

Of the embodiments described, treating cancer cells with 3-(2-bromoethyl) indole has been shown to have greater bioactivity on cancer cells than that of known indole-3-carbinol. As used herein, 3-(2-bromoethyl) indole means an indole compound having the structure of formula (I), wherein $R_1$ represents bromine. For purposes of this application, 3-(2-bromoethyl) indole may be referred to as "BEI-9" in both this detailed description and the drawings. As discussed in Example 1 herein, 3-(2-bromoethyl) indole has proven to have a more potent bioactivity than known indole-3-carbinol when both are used to treat cancer cells. Moreover, as discussed in Examples 2-4 herein, 3-(2-bromoethyl) markedly inhibits cell proliferation, even when treating cancer cells with a 12.5 µM concentration of 3-(2-bromoethyl) indole. Further, treating SW480 colon cancer cells with 3-(2-bromoethyl) indole has been shown to have a residual effect, inhibiting cell recovery after treatment even after the compound has been washed away.

According to further embodiments, the present invention provides a method of killing cancer cells by treating cancer cells with a 3-(2-substituted-ethyl) indole compound, or the pharmaceutically acceptable salt thereof, having the structure of formula (I) wherein R is selected from the group consisting of: a halogen, aldehyde, alkyl, hydroxyalkyl, carboxyl, carboxyalkyl, benzyl, benzylakyl, sulfonate, alkyl sulfonate, and sulfonamide. In a related aspect, the present invention provides for a method of killing cancer cells by treating cancer cells with a 3-(2-substituted-ethyl) indole having the structure of formula (I), wherein R represents bromine. According to the teachings described herein, the embodiments of the present invention have been shown to be particularly effective at inhibiting colon cancer cell growth and motility.

EXAMPLES

The following examples describe specific aspects of the invention to illustrate its utility and novelty. Moreover, they provide a description of methods and results used to identify the inhibiting effect the present invention has on the proliferation and viability of cancer cells. The examples should not be construed as limiting the invention in any manner and are provided exclusively to aid those of skill in the art in understanding and practicing the invention.

Example 1: 3-(2-bromoethyl) indole is more potent than indole-3-carbinol

SW480 colon cancer cells were treated with solvent DMSO (CONT), staurosporine (STS)—an agent that is known to kill cancer cells—and four select indole derivative compounds. Cell viability and proliferation was examined under a MTT assay protocol. FIG. 1A shows the relative viability/proliferation index of the select indole compounds as compared to the control solvent. The control solvent is shown as in FIG. 1A as the bar corresponding to "CONT." When treated with only the control solvent, the cancer cells are 100% viable. Yet, according to FIG. 1A, treating cancer cells with 3-(2-bromoethyl) indole reduces cancer cell viability and proliferation by about 60% within 48 hours. As noted in FIG. 1A, 3-(2-bromoethyl) indole is represented by "INDOLE 9." By comparison, a similar concentration of indole-3-carbinol reduces cell proliferation only by about 30%. As noted in FIG. 1A, indole-3-carbinol is represented by "INDOLE 14."

Example 2: 3-(2-Bromoethyl) Indole Markedly Inhibits Cell Proliferation

Figure 2:
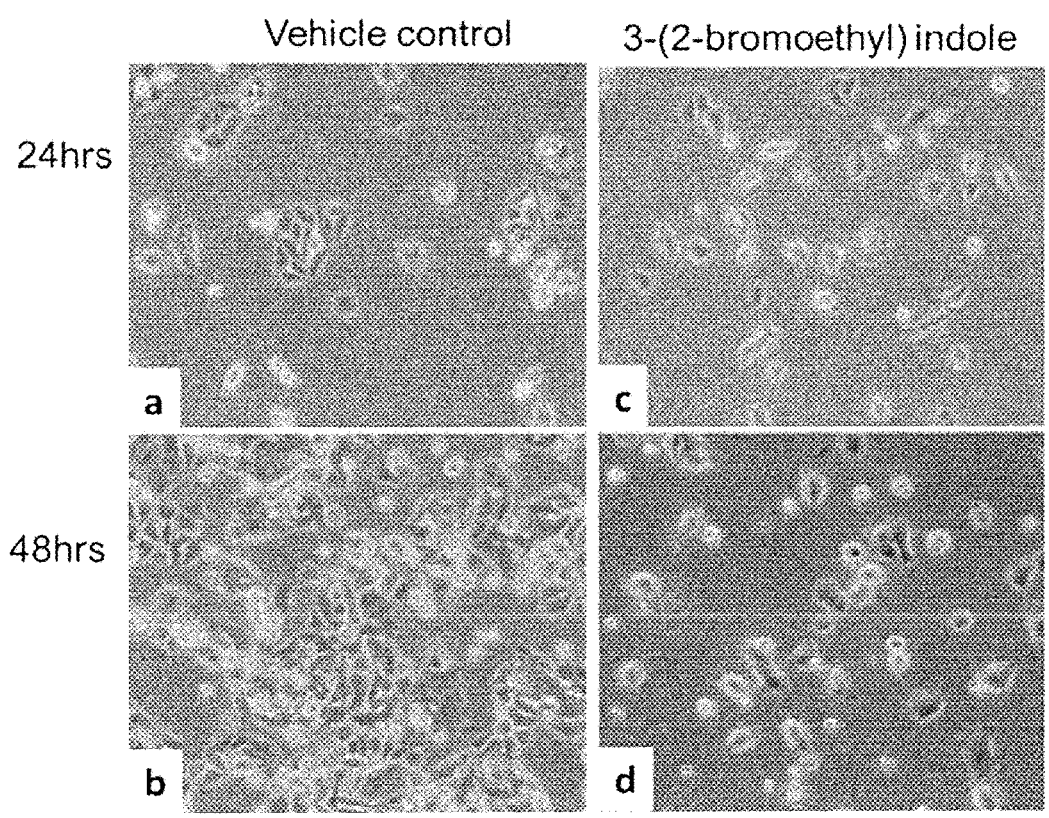
FIG. 2 shows microphotographs that were taken 24 hours and 48 hours after SW480 colon cancer cells were treated with either vehicle (DMSO) or 25 µM 3-(2-bromoethyl) indole, as discussed in Example 2 herein.
Figure 3A:
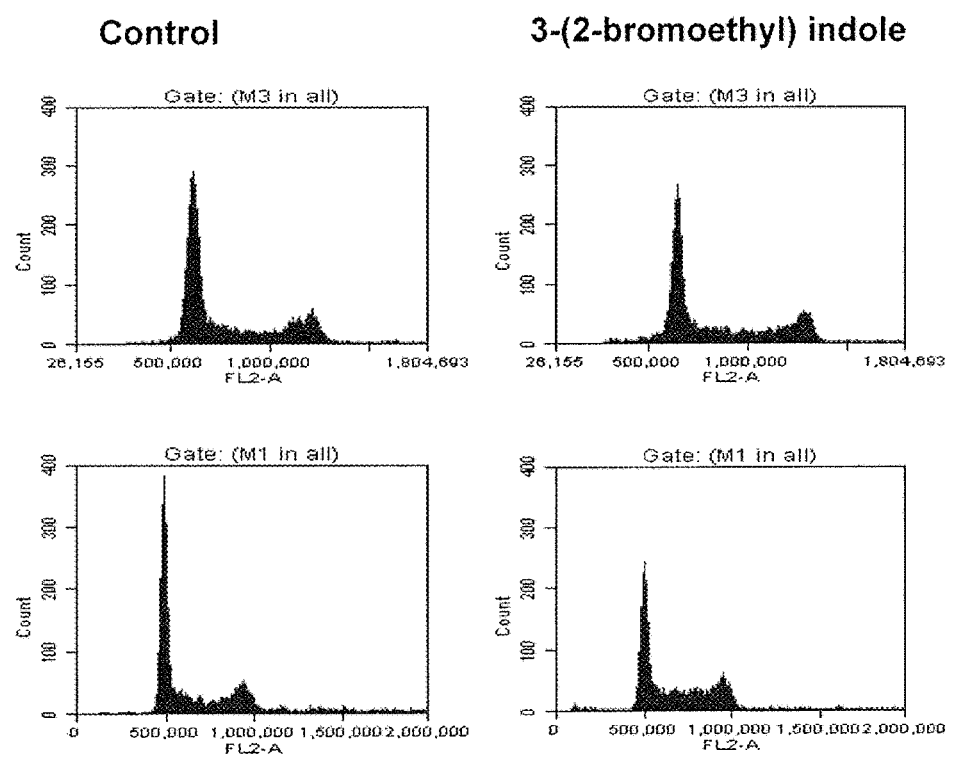
FIG. 3A illustrates the results of a cell cycle analysis performed on SW480 cancer cells that were treated with a control and 3-(2-bromoethyl) indole. The cell cycle analysis includes snapshots of the cells at 24 and 48 hours after treatment. This shows no apparent induction of sub-G1 population of cells indicative of apoptosis.
Figure 3B:
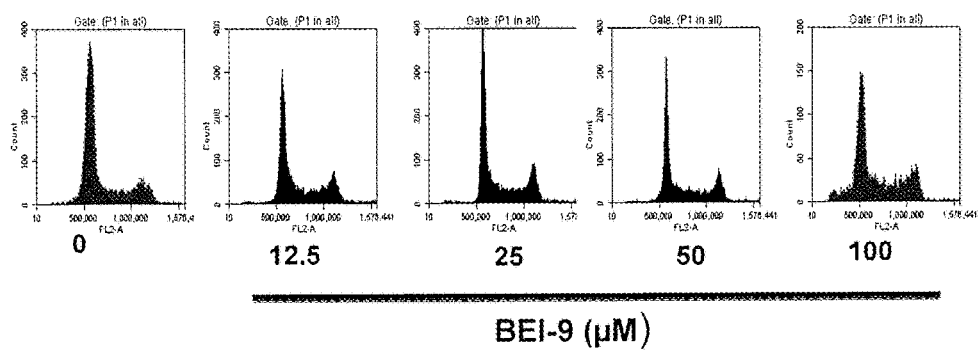
FIG. 3B illustrates the results of a cell cycle analysis performed on SW480 cancer cells that were treated with variable concentrations of 3-(2-bromoethyl) indole. Cell death is noticed at the highest concentration of 3-(2-bromoethyl) indole that was tested (100 µM).

SW480 colon cancer cells were treated with either vehicle control (DMSO) or 25 μM 3-(2-bromoethyl) indole. As shown in FIG. 2, microscopic evaluation of treated cells revealed that 3-(2-bromoethyl) indole-treated cells failed to multiply and populate the cell culture dish surface. By comparison, vehicle-treated cells rapidly proliferated and visibly filled the surface on which they were seeded. Microphotographs were taken 24 hours (a and c) and 48 hours (b and d) after the treatments. FIG. 2 indicates that the vehicle-treated control cells multiplied and filled out the growth surface, whereas those treated with 3-(2-bromoethyl) indole did not show any sign of proliferation, thus evidencing the growth inhibitory activity of the 3-(2-bromoethyl) indole. To further examine the possibility of inhibited cell proliferation, cell cycle analysis was performed by flow cytometry on cells that were treated with 50 μM 3-(2-bromoethyl) indole for 24 and 48 hours. In agreement with the results detailed in FIG. 2, the results of the cell cycle analysis suggest that treating cells with a 3-(2-substituted) indole compound markedly inhibits cell proliferation. In fact, the specific effect of treating cells with 3-(2-bromoethyl) was to "freeze" the cell growth during treatment. This is illustrated in FIG. 3. As can be seen, the cell cycle profiles of cells treated with 3-(2-bromoethyl) indole were nearly indistinguishable at 24 hours post treatment and 48 hours post treatment. By comparison, the cells that were treated solely with vehicle control solvent dramatically increased from 24 hours after treatment to 48 hours after treatment. Therefore, FIG. 3 further evidences that treating cancer cells with 3(2-bromoethyl) indole effectively prevents proliferation of such cancer cells.

Example 3: Bioactivity Depends on the Dose of 3-(2-Bromoethyl) Indole

Figure 4:
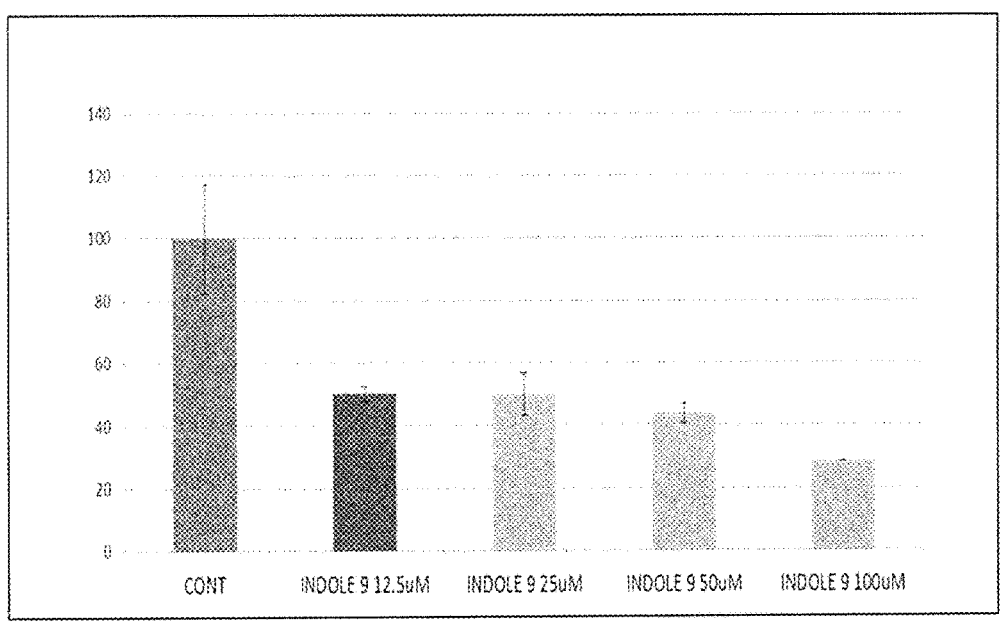
FIG. 4 shows that the bioactivity of 3-(2-bromoethyl) indole is directly related to the concentration of the compound used to treat the cancer cells, as discussed in Example 3 herein.
Figure 5:
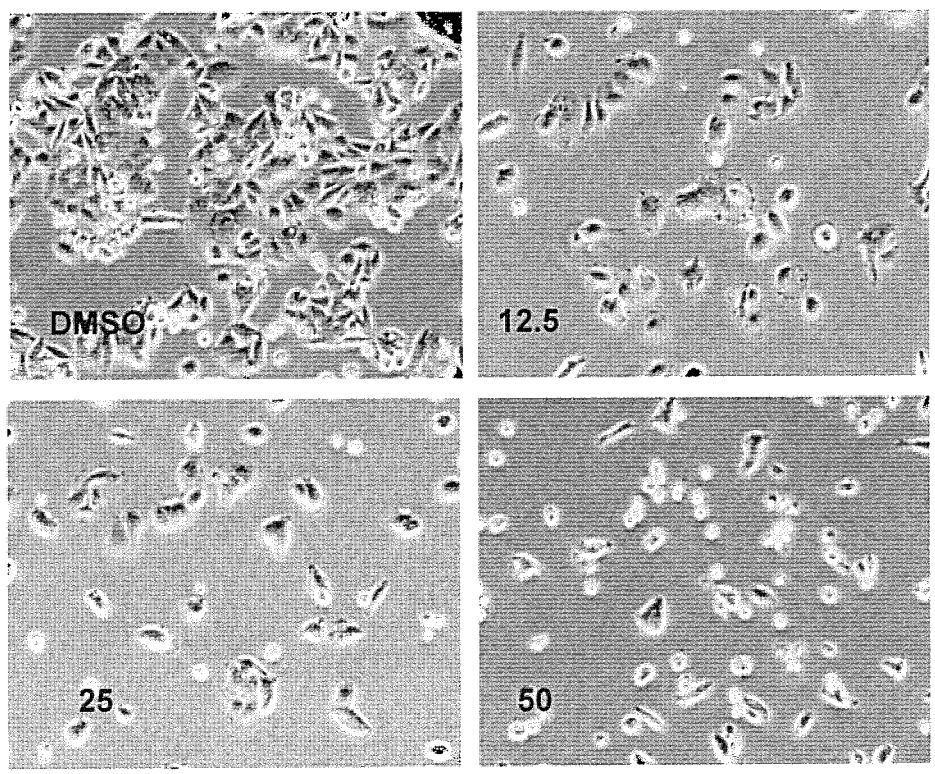
FIG. 5 shows the results of a dose response examination of SW480 cancer cells that are treated with 3-(2-bromoethyl) indole at variable concentrations. The top left microphotograph shows cells treated with the control vehicle (DMSO), while the other three microphotographs show cells treated with 12.5 µM, 25 µM, and 50 µM 3-(2-bromoethyl) indole.

Increasing concentrations of 3-(2-bromoethyl) indole (from 12.5 μM to 100 μM) were tested on SW480 colon cancer cells, and viability of the treated cells was measured by the CellTiter-Glo® (Promega® Corporation) method. FIG. 4 shows that marked (about 50%) reduction in cell viability was attained even when merely treating SW480 cancer cells with 12.5 μM 3-(2-bromoethyl) indole. The fact that the lowest concentration tested exhibited a marked reduction in cancer cell viability indicates a strong bioactivity of the compound. Similarly, dose response examination and cell cycle analysis using variable concentrations of 3-(2-bromoethyl) indole ranging from 12.5 to 100 μM confirms that even doses lower than 50 μM inhibit cell proliferation. See FIGS. 3B and 5. Thus, useful embodiments of the present invention provide for a method of inhibiting cancer cell proliferation, comprising treating the cancer cells with 3-(2-bromoethyl) indole with concentrations of greater than or equal to 0.2 μM, or in a range of 1.0 μM to 50.0 μM, or more specifically, from 5.0 μM to 25.0 μM.

Figure 6:
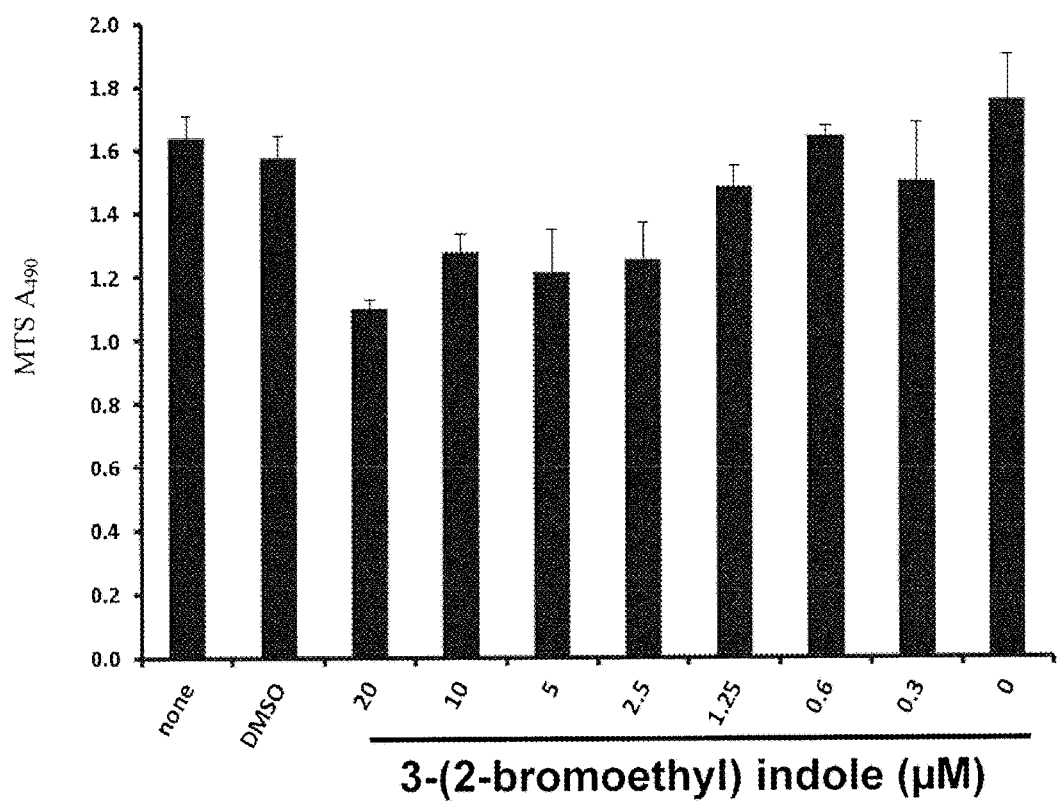
FIG. 6 shows the results of a dose response examination of HCT116 cancer cells that are treated with 3-(2-bromoethyl) indole at variable concentrations.
Figure 7:
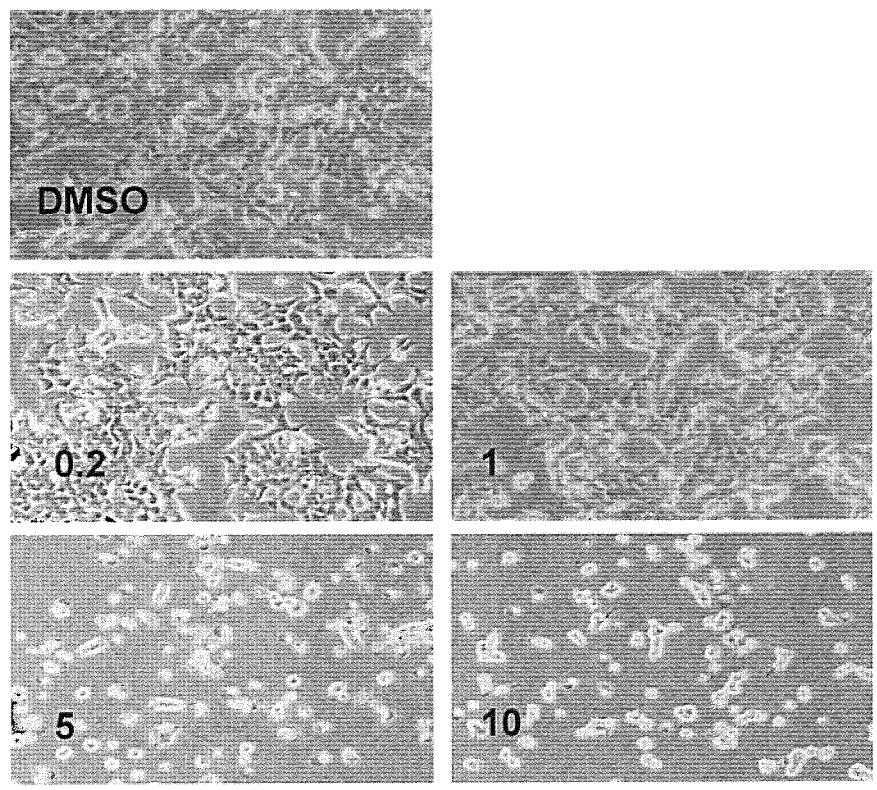
FIG. 7 shows the results of a dose response examination of HCT116 cancer cells that were treated with 3-(2-bromoethyl) indole at variable concentrations. The top left microphotograph shows cells treated with the control vehicle (DMSO), while the other four microphotographs show cells treated with 0.2 µM, 1.0 µM, 5.0 µM, and 10 µM 3-(2-bromoethyl) indole. The results indicate that even low doses (e.g., 5.0 µM of 3-(2-bromoethyl) indole effectively block the proliferation of cancer cells.

The activity of 3-(2-bromoethyl) indole on another colon cancer cell line, HCT116, was also tested. Similar to its effects on SW480 cancer cells, 3-(2-bromoethyl) indole decreased the viability index of HCT116 cells, as measured by MTS assay. The results of this assay are shown in FIG. 6. The absorbance reading at a wavelength of 490 nm is shown on the Y-axis. Moreover, FIG. 7 shows that 3-(2-bromoethyl) indole treatment completely stopped the proliferation of HCT116 cells at 5 μM and 10 μM concentrations.

Figure 8:
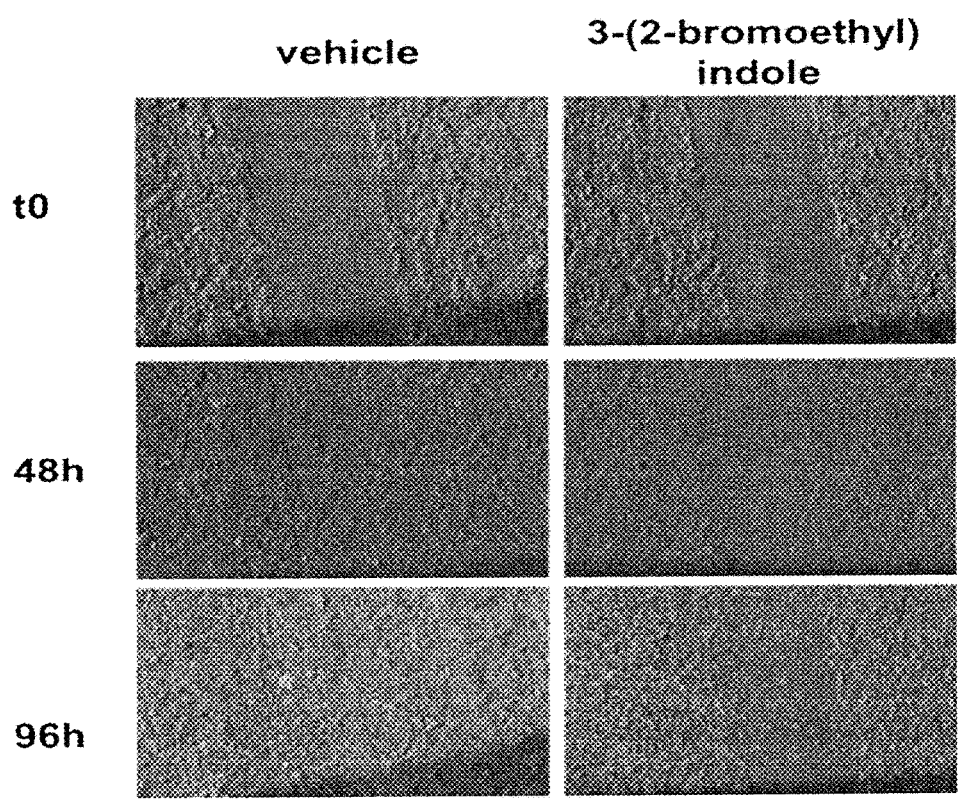
FIGS. 8 and 9 show the results of a scratch wound healing assay, as discussed in Example 4 herein. Confluent SW480 colon cancer cells were scratched with a pipette tip to create wounded cells, and the wounded cells were then treated with either vehicle (DMSO) or 25 µM 3-(2-bromoethyl) indole. The ability of the cells to migrate and fill the gap was followed by light microscopy imaging at 24-hour intervals.
Figure 9:
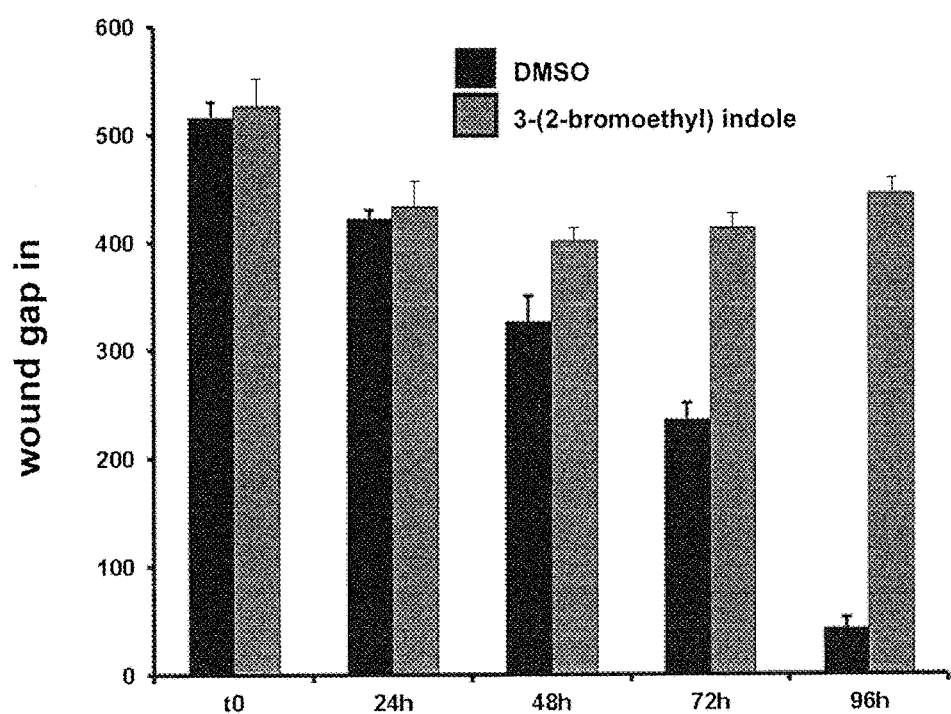

Example 4: The Effect of 3-(2-Bromoethyl) Indole on the Motility of SW480 Cancer Cells Scratch wound healing assay was performed on SW480 cells grown to confluence. Confluent SW480 cells were scratched with a pipette tip to create cell wounds, which were treated with vehicle control solvent (DMSO) and 25 μM 3-(2-bromoethyl) indole. The ability of the cells to migrate and fill the gap created by the scratch was evaluated. Results show that 3-(2-bromoethyl) indole markedly inhibited the motility of SW480 cells. By comparison, vehicle-treated cells filled the scratch within 96 hours. FIG. 8 shows the results of the scratch wound healing assay. The ability of the cells to migrate and fill the gap was followed by light microscopy imaging at 24-hour intervals. FIG. 8 shows microphotographs taken at the beginning of the experiment (t0), at 48, and at 96 hours after the treatment. The scratch wound is most visible as a clear space at t0. FIG. 9 further shows that vehicle-treated cells migrated and almost fully closed the wound gap within 96 hours—as anticipated. By comparison, 3-(2-bromoethyl) indole treated cells failed to migrate and close the wound gap. Only a few single cells treated with 3-(2-bromoethyl) indole were visible and scattered in the gap. Moreover, there was no evidence of cell division. The results of the scratch wound healing assay shown in FIGS. 8 and 9 indicate that 3-(2-bromoethyl) indole potently inhibits the migratory capacity of treated cells.

Example 5: Residual Effect of 3-(2-Bromoethyl) Indole on SW480 Cancer Cells

To examine if treated cells would recover after the compound was washed out, SW480 colon cancer cells were treated with 25 μM 3-(2-bromoethyl) indole for 48 hours, then the monolayer was rinsed 3 times with culture medium to remove the compound. The cell monolayers were left in the fresh growth medium for four days of further incubation.

Figure 10:
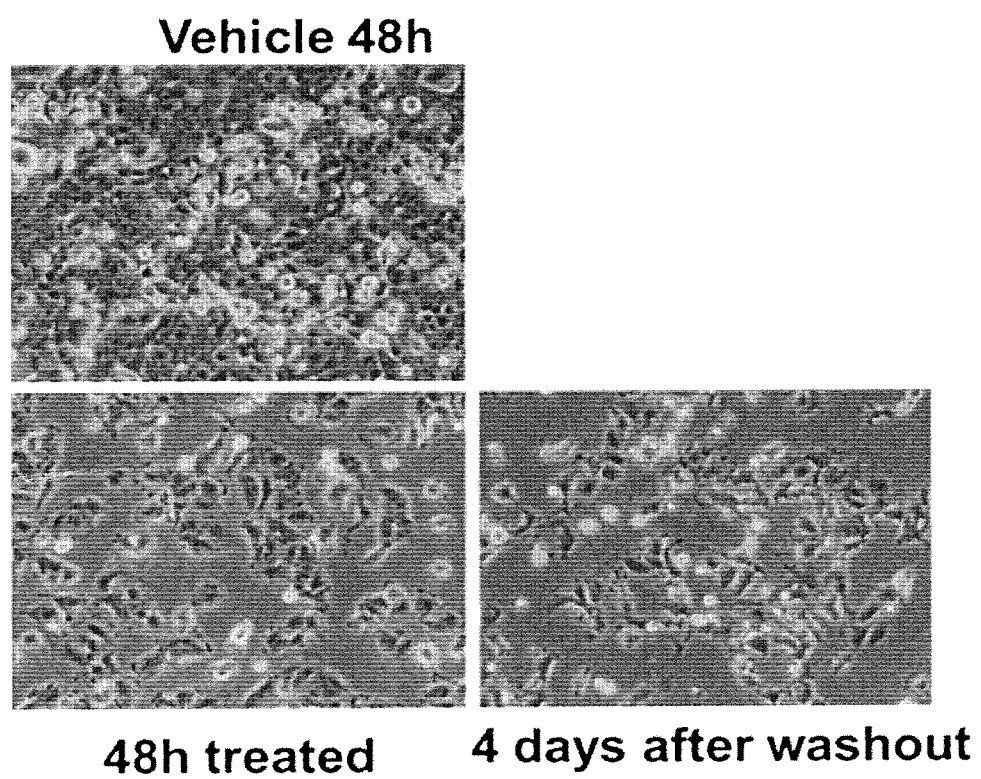
FIG. 10 shows the residual effect of 3-(2-bromoethyl) indole on SW480 cancer cells, as discussed in Example 5 herein. SW480 colon cancer cells failed to recover from being treated with 3-(2-bromoethyl) indole. 48 hours after seeding, vehicle-treated cells were confluent (top panel), whereas 3-(2-bromoethyl) indole-treated cells were still arrested from proliferation (lower left panel). 3-(2-bromoethyl) indole was washed out and cells were monitored for an additional four days, with the growth medium being changed every second day.

Results shown in FIG. 10 reveal that the vehicle-treated SW480 cells rapidly grew to full confluency in just 48 hours. By comparison, the cells treated with 3-(2-bromoethyl) indole were not able to recover at all after a mere single treatment, even four days after the 3-(2-bromoethyl) indole had been washed from the growth medium.

Example 6: 3-(2-Bromoethyl) Indole Efficiently Down-Regulates Cyclin D1

Figure 11:
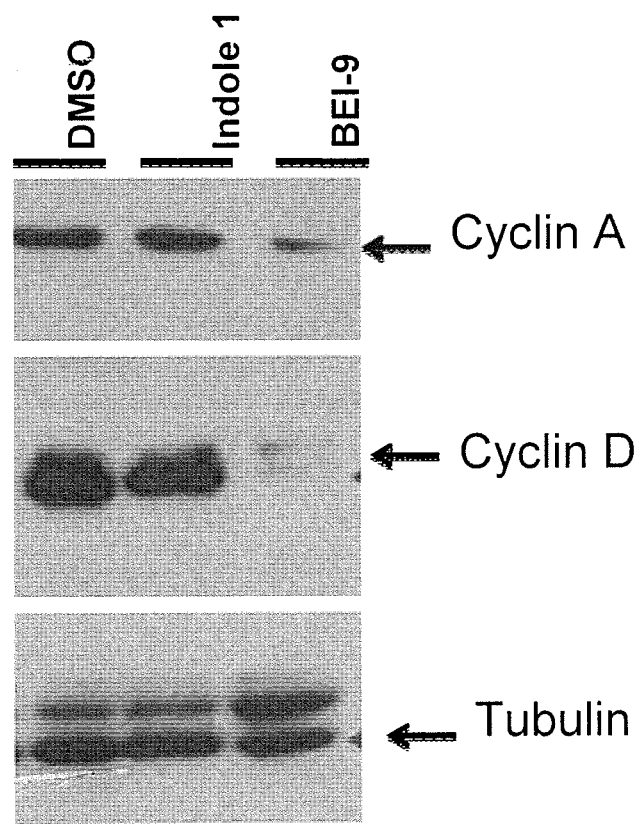
FIG. 11 shows cell cycle progression for cyclin A protein, cyclin D protein, and tubulin protein, which were all treated with control vehicle (DMSO), indole compound 1 (5-methoxyindole), and 3-(2-bromoethyl) indole.

Progression through the cell cycle is regulated by cyclins and their enzyme partner, cyclin dependent kinases (CDK). The regulation of the cyclin-CDK pair activity is controlled by synthesis and degradation of the cyclin moiety. Cyclin D1 is one of the regulatory cyclins involved in the G1-S transition of cells, and is a known oncogene. As cyclin D1 is a key regulator of cell cycle progression, levels of cyclin D1 protein in both control cells and treated cells were assessed by immunoblotting. Also assessed were the levels of cyclin A, another cyclin regulating both G1-S as well as G2-M transitions. The results, shown in FIG. 11, reveal that treatment with 3-(2-bromoethyl) indole drastically decreased the expression of cyclin D1 protein, as well as that of cyclin A. FIG. 11 shows that 3-(2-bromoethyl) indole treatment inhibits the expression of cyclins, which drive the key transitions in cancer cell proliferation. Accordingly, inhibiting the expression of cyclins likely contributes to the observed "freezing" effect described previously. Referring to FIG. 11, "indole 1" represents 5-methoxyindole, which did not exhibit the same beneficial effects as 3-(2-bromoethyl) indole.

Example 7: Effect of 3-(2-Bromoethyl) Indole on Inhibiting NF-kB Signaling

One of the regulators of cyclin D1 is the multifunctional transcription factor NF-kB. The effect of 3-(2-bromoethyl) indole on NF-kB signaling was also examined. The inventors were motivated to test the effects of 3-(2-bromoethyl) indole on NF-kB signaling because of the marked reduction of cyclin D1 expression in SW480 cells treated with 3-(2-bromoethyl) indole (as seen in FIG. 11) and the relation of cyclin D1 and NF-kB. In carrying out the test, NF-kB reporter SW480 cells (SW-NFL) were used. The cells were stably transduced with a construct containing NF-kB-responce elements linked to the luciferase gene as the reporter. Previous work has shown that these cells activate NF-kB in response to TNFα, as well as some clinically used chemotherapeutic drugs. As an experimental response to NF-kB activation, these cells express increased amounts of luciferase enzyme, which can be detected by luminescence assay.

Figure 12:
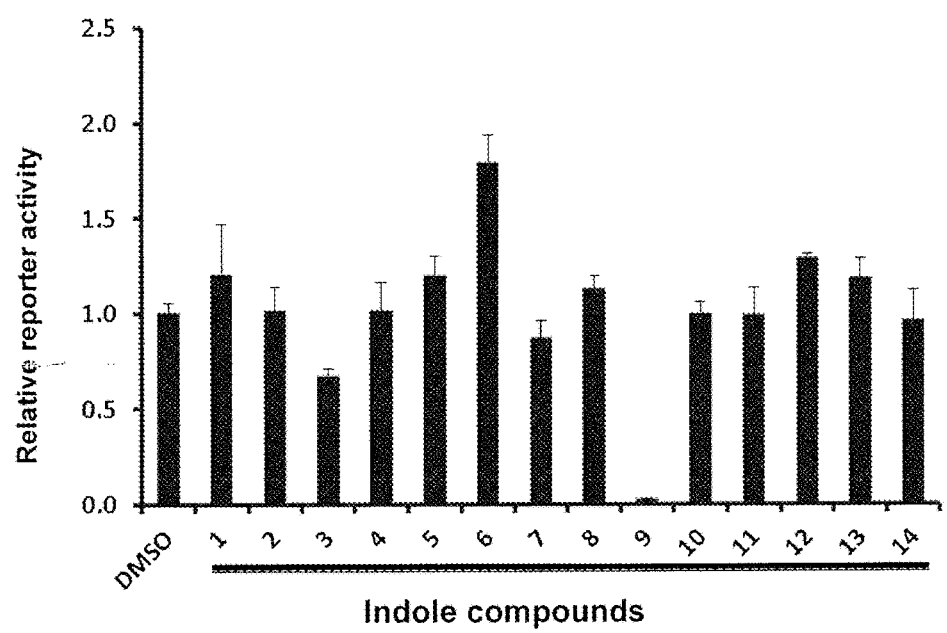
FIG. 12 shows the effect of the fourteen tested indole compounds on luciferase enzyme activity.

First, the effect of 3-(2-bromoethyl) indole and each of the thirteen other indole compounds on the basal levels of luciferase activity was assessed. An equal number of SW480-NFL cells seeded in a 96-well plate were treated with control vehicle (DMSO) or one of the fourteen indole-derivative test compounds. Luciferase enzyme activity was measured 24 hours after the treatment. Results clearly indicate that among the 14 compounds, only 3-(2-bromoethyl) indole reduced the reporter activity. See FIG. 12, where BEI-9 is the 9th indole test sample depicted in the graph.

Figure 13:
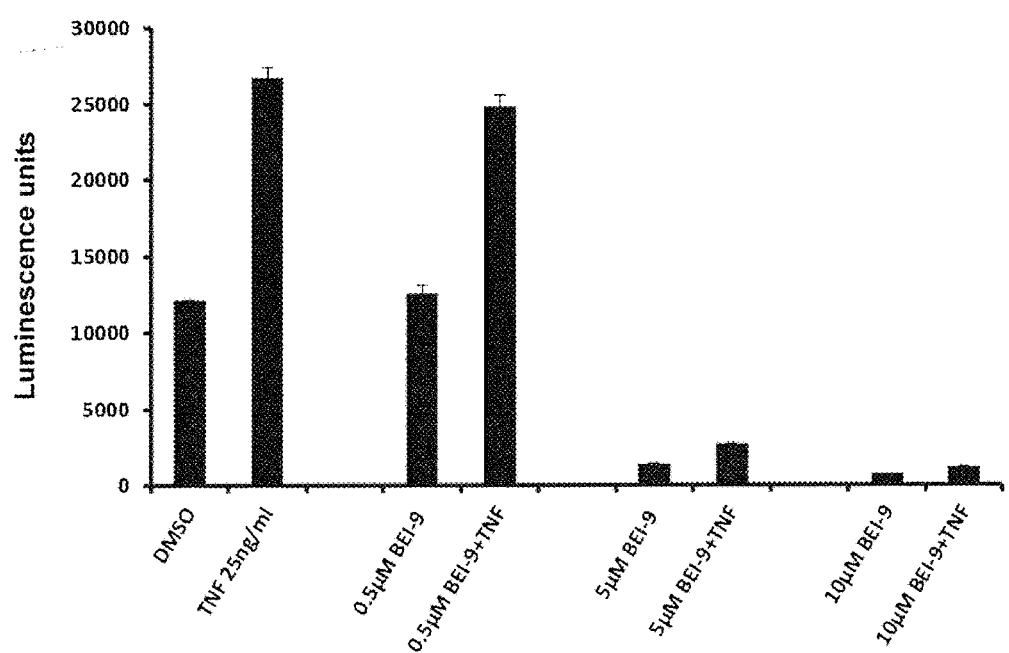
FIG. 13 shows whether cytokine-induced NF-kB activation can be blocked by 3-(2-bromoethyl) indole treatment. TNFα was used to activate NF-kB in reporter cells, and then the cells were co-treated with variable amounts of 3-(2-bromoethyl) indole.
Figure 14:
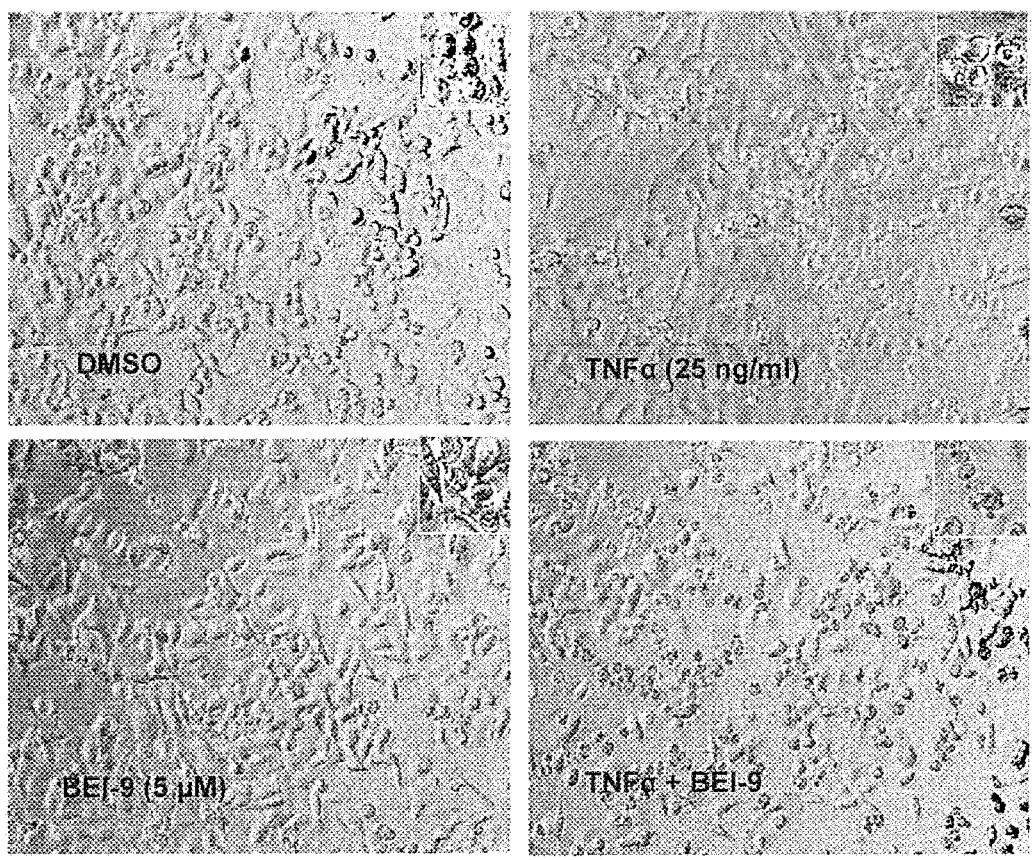
FIG. 14 shows that a treatment of either TNFα or 3-(2-bromoethyl) indole, alone, fails to indicate any sign of cell apoptosis. Microphotographs were taken of SW480 cells treated with vehicle control (DMSO) (top left), 25 ng/ml TNFα (top right), 5 µM 3-(2-bromoethyl) indole (bottom left), and a combination of 25 ng/ml TNFα and 5 µM 3-(2-bromoethyl) indole (bottom right).

Second, it was determined whether cytokine-induced NF-kB activation can be blocked by 3-(2-bromoethyl) indole. In prior studies, SW480-NFL cells were tested and confirmed as being responsive to TNFα, a canonical NF-kB pathway inducer, and various clinical chemotherapeutic drugs. To this end, TNFα was first used to activate NF-kB in these reporter cells. It was examined whether co-treatment would interfere with activation of the NF-kB pathway. SW480-NFL cells were treated with 25 ng/ml TNFα as an activator, and with 0.5 µM, 5 µM, or 10 µM BEI-9 as test compound. As shown in FIG. 13, a treatment of 5 µM or 10 µM 3-(2-bromoethyl) indole completely abolished the activation of NF-kB reporter activity by TNFα. The apparent difference between the effects of 0.5 µM and 5 µM 3-(2-bromoethyl) indole is over 10 fold, suggesting a low micromolar range of effective concentration of 3-(2-bromoethyl) indole in SW480 colon cancer cells. Moreover, although neither of the two compounds (TNFα and 3-(2-bromoethyl) indole) as single agents caused cell death, the combination of 25 ng/ml TNFα and 5 µM 3-(2-bromoethyl) indole resulted in the appearance of cells with membrane blebs, which is typical of apoptosis. The effect of such a combination treatment is shown in the bottom left microphotograph in FIG. 14. Referring to FIG. 14, microphotographs were taken of SW480 cells treated with vehicle control (DMSO) (top left), 25 ng/ml TNFα (top right), 5 µM 3-(2-bromoethyl) indole (bottom left), and a combination of 25 ng/ml TNFα and 5 µM 3-(2-bromoethyl) indole (bottom right). Accordingly, in addition to inhibiting NF-kB activation, the addition of 3-(2-bromoethyl) indole to TNFα treated cells may divert TNF receptor-initiated receptor signaling towards apoptosis.

Figure 15A:
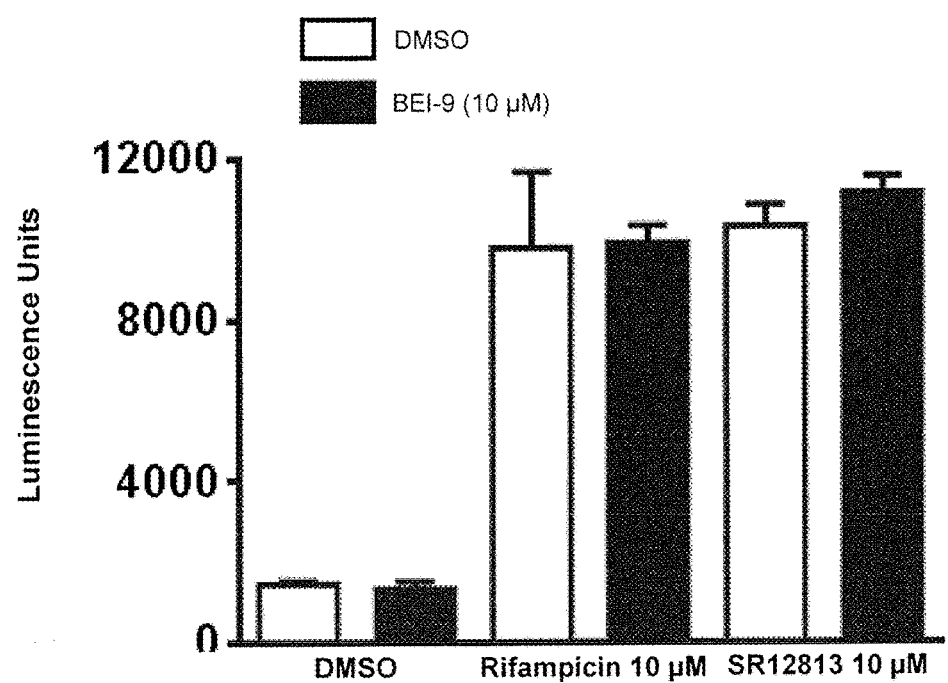
FIGS. 15A and 15B show that 3-(2-bromoethyl) indole does not compete with cellular ATP, and thus, does not inhibit luciferase activity. A PXR-luciferase reporter system expressed in HepG2 cells was used to perform a luciferase assay. 10 µM BEI-9 was added to reporter cells 5 minutes before measuring luciferase catalyzed reactions. As the luminescence activity is roughly the same for cells treated with the control as those treated with BEI-9, FIG. 15A suggests that BEI-9 does not inhibit luciferase by competing with ATP.
Figure 15B:
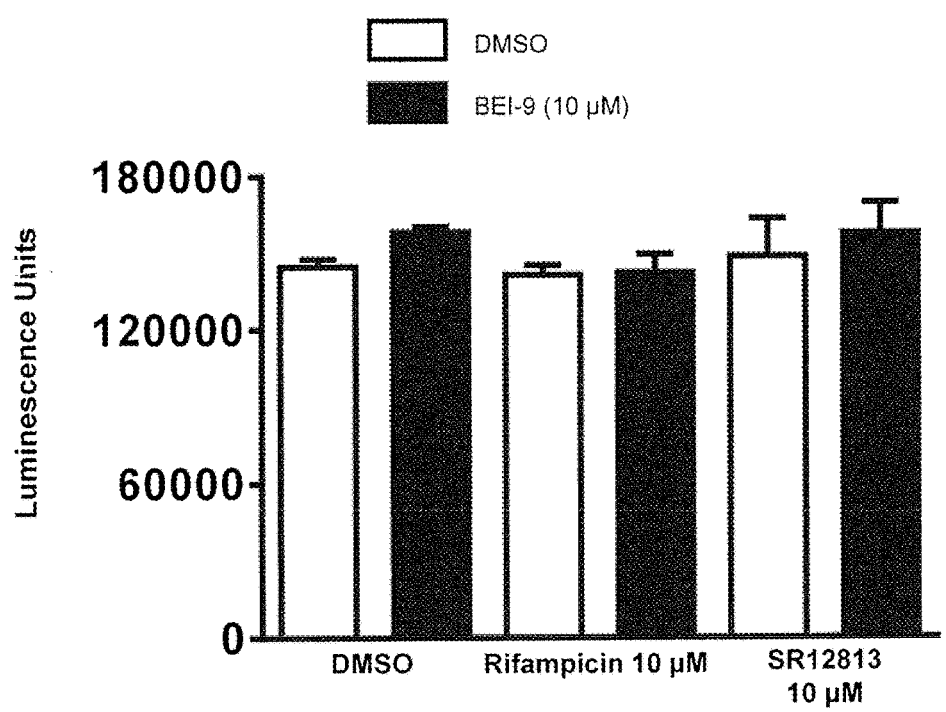

Luciferase reporter assays are dependent on the activity of the luciferase enzyme to catalyze the conversion of luciferin to oxyluciferin in the presence of ATP and oxygen, generating light in the process. Therefore, compounds that may directly interfere with the enzyme activity should be distinguished from those that inhibit the signaling activity reported inside the cells. To test this, a PXR-luciferase reporter system expressed in HepG2 cells was used and a luciferase assay was performed by adding 10 µM BEI-9 to the cells five minutes before measuring luciferase catalyzed reactions. In parallel, ATP-dependent cell viability was also measured using a CellTiter-Glo® kit to examine if BEI-9 would compete with cellular ATP, which is required for the luciferase activity. The results from both assays, shown in FIGS. 15A-15B suggest that at the bioactive concentration tested (10 µM), BEI-9 does not inhibit luciferase directly or indirectly by competing with ATP.

Figure 16:
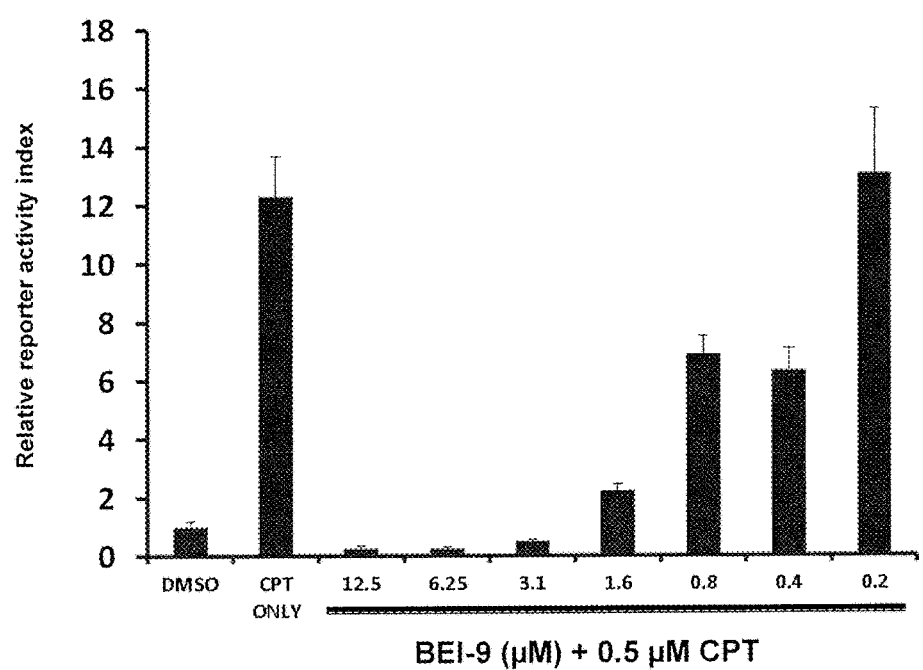
FIG. 16 shows that SW480 cancer cells that were treated with a combination of 0.5 µM camptothecin and variable concentrations of 3-(2-bromoethyl) indole can suppress drug-induced NF-kB response in such cells.

In prior art, it has been shown that camptothecin (also referred to herein as "CPT"), one of adjuvant drugs clinically used to treat various types of cancers, activates NF-kB in SW480 reporter cells at peak activating concentrations of 0.5 µM or 1.0 µM. The consequence of NF-kB activation as a result of treatment with adjuvant chemotherapy drugs is still under study. To examine whether a combination of CPT with BEI-9 suppresses a drug-induced NF-kB response in SW480 reporter cells, such cells were treated with 0.5 µM CPT and varying concentrations (0.2 µM-12.5 µM) of BEI-9. Results from this experiment show that BEI-9 inhibits the NF-kB response by more than 50% at concentrations greater than 0.8 µM, as compared to CPT-only treatment. See FIG. 16. Among the tested concentrations, only 0.2 µM did not have any noticeable effect on the reporter activity. This suggests that a sub-micromolar concentration of BEI-9 is an effective inhibitor of CPT-induced NF-kB response.

Figure 17:
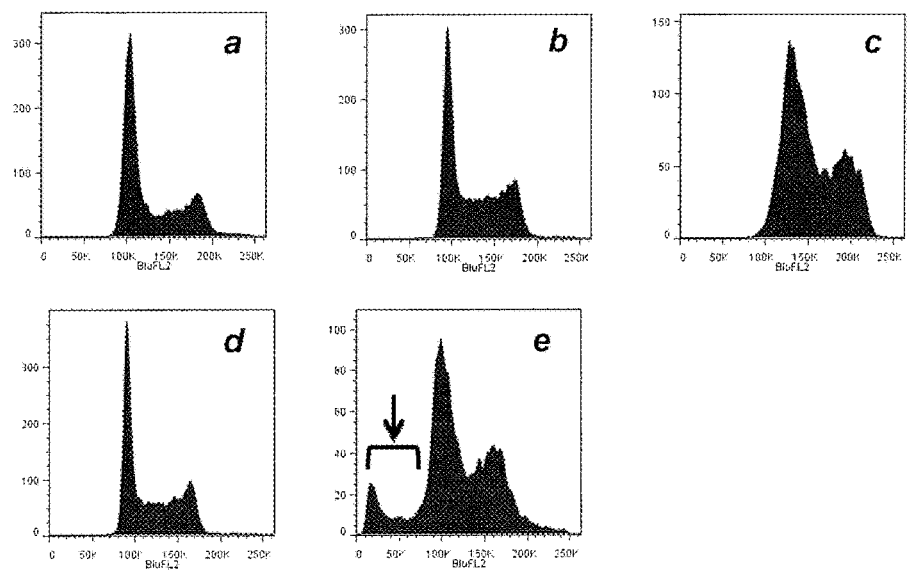
FIG. 17 shows flow cytometry results of combining camptothecin and varying concentrations of 3-(2-bromoethyl) indole to treat SW480 cancer cells. Cell cycle profiles of SW480 cells treated with DMSO (a), 3-(2-bromoethyl) indole (b), camptothecin (c), 3-(2-bromoethyl) indole and camptothecin co-treatment (d), or 24 hours of camptothecin treatment followed by 24 hours of only 3-(2-bromoethyl) indole treatment (e). The flow cytometry results indicate that the combination treatment of camptothecin and 3-(2-bromoethyl) indole may exhibit signs of cell apoptosis. The short arrow points to the sub-G1 population of cells resulting from the combination treatment. Sequential treatment of camptothecin for 24 hours followed by BEI-9 for 24 hours resulted in the appearance of a distinct sub-G1 population, as shown in FIG. 17(e). These results suggest that sequential treatment can induce cancer cell apoptosis.

It was also examined by flow cytometry whether the combination of CPT and BEI-9 would induce cell apoptosis as measured by accumulation of sub-G1 population. Interestingly, while single agent or co-treatment of CPT and BEI-9 did not induce apoptosis in these cells, sequential treatment of CPT for 24 hours followed by BEI-9 for 24 hours resulted in the appearance of a distinct sub-G1 population. The results of this test are shown in FIG. 17. Referring to FIG. 17, cell cycle profiles of parental SW480 cells treated with DMSO (a), BEI-9 (b), CPT (c), BEI-9 and CPT co-treatment (d) or 24 hours of CPT followed by 24 hours of only BEI-9 (e) are shown. The short arrow points to the sub-G1 population of cells resulting from the combination treatment. Sequential treatment of camptothecin for 24 hours followed by BEI-9 for 24 hours resulted in the appearance of a distinct sub-G1 population, as shown in FIG. 17(e). These results suggest that sequential treatment can induce cancer cell apoptosis.

These results are important because the potential synergy between CPT and BEI-9 appears to be dependent on the sequence of treatments. This theory is in accordance with the different mechanisms and dynamics of actions of TNFα and CPT; the slow CPT-induced cellular effects could be easily overcome by the anti-cellular proliferation effects of BEI-9, while the rapid receptor effects of TNFα could be modulated by BEI-9 as a second step. However, when CPT was given time to act on the cells, subsequent addition of BEI-9 appeared to induce cell apoptosis.

What is claimed is:

1. A method of inhibiting cancer cell proliferation, comprising treating cancer cells with 3-(2-bromoethyl) indole or a pharmaceutically acceptable salt thereof, wherein the treated cancer cells are inhibited from proliferation as compared to non-treated cancer cells; and wherein the cancer cells are colon cancer cells.

2. A method of killing colon cancer cells, comprising:
treating the colon cancer cells with a combination of TNFα and 3-(2-bromoethyl) indole.

3. The method of claim 2, wherein the 3-(2-bromoethyl) indole is administered at a concentration of at least 0.8 uM.

4. A method of killing colon cancer cells comprising:
treating the colon cancer cells with a combination of one or more chemotherapeutic drugs and 3-(2-bromoethyl) indole.

5. The method of claim 4, wherein the one or more chemotherapeutic drugs is camptothecin or a camptothecin-analog.

6. The method of claim 5, wherein the camptothecin-analog is chosen from the group consisting of topotecan and irinotecan.

7. The method of claim 4, wherein the cancer cells are treated firstly with the one or more chemotherapeutic drugs, and after a predetermined waiting period, treated secondly with 3-(2-bromoethyl) indole.

8. The method of claim 7, wherein the predetermined waiting period is at least 24 hours.

9. A method of reducing NF-kB activation in colon cancer cells, comprising treating colon cancer cells with 3-(2-bromoethyl) indole.

* * * * *